United States Patent
Malecha

(10) Patent No.: US 10,371,660 B2
(45) Date of Patent: Aug. 6, 2019

(54) ACCURATE ANALYTE MEASUREMENTS FOR ELECTROCHEMICAL TEST STRIP BASED ON MULTIPLE CALIBRATION PARAMETERS

(71) Applicant: Lifescan IP Holdings, LLC, Wayne, PA (US)

(72) Inventor: Michael Malecha, Muir of Ord (GB)

(73) Assignee: LifeScan IP Holdings, LLC, Malvern, PA (US)

( * ) Notice: Subject to any disclaimer, the term of this patent is extended or adjusted under 35 U.S.C. 154(b) by 1008 days.

(21) Appl. No.: 13/896,986

(22) Filed: May 17, 2013

(65) Prior Publication Data

US 2014/0339100 A1 Nov. 20, 2014

Related U.S. Application Data

(60) Provisional application No. 61/824,549, filed on May 17, 2013.

(51) Int. Cl.
*G01N 27/327* (2006.01)
*G01N 33/487* (2006.01)

(52) U.S. Cl.
CPC ..... *G01N 27/3275* (2013.01); *G01N 27/3274* (2013.01); *G01N 33/48771* (2013.01)

(58) Field of Classification Search
CPC ... G01N 27/327; G01N 27/3271–3275; G01N 33/48771
See application file for complete search history.

(56) References Cited

U.S. PATENT DOCUMENTS

| | | |
|---|---|---|
| 5,708,247 A | 1/1998 | McAleer et al. |
| 5,951,836 A | 9/1999 | McAleer et al. |
| 6,241,862 B1 | 6/2001 | McAleer et al. |
| 6,284,125 B1 | 9/2001 | Hodges et al. |
| 6,733,655 B1 | 5/2004 | Davies et al. |
| 8,358,210 B2 | 1/2013 | Goodnow et al. |
| 8,390,455 B2 | 3/2013 | Goodnow et al. |
| 8,410,939 B2 | 4/2013 | Goodnow et al. |
| 2006/0003462 A1* | 1/2006 | Wang ............... G01N 33/48771 436/149 |
| 2010/0148972 A1 | 6/2010 | Goodnow et al. |
| 2012/0305419 A1 | 12/2012 | Singhal |

FOREIGN PATENT DOCUMENTS

| | | | |
|---|---|---|---|
| EP | 1825806 A2 | 8/2007 | |
| WO | WO 2006/040200 A1 | 4/2006 | |
| WO | 2006086423 A2 | 8/2006 | |
| WO | WO 2006/086423 A2 * | 8/2006 | ............. G08B 13/14 |
| WO | 2012164271 A1 | 12/2012 | |
| WO | 2013030375 A1 | 3/2013 | |
| WO | WO 2013/098563 A1 | 7/2013 | |
| WO | WO 2013/098564 A1 | 7/2013 | |
| WO | WO 2013/098565 A1 | 7/2013 | |

OTHER PUBLICATIONS

European Search Report issued in related European Patent Application No. 14168696.4, dated Aug. 27, 2014, 9 pages.

* cited by examiner

*Primary Examiner* — Gurpreet Kaur
*Assistant Examiner* — Steven E Rosenwald

(57) ABSTRACT

Various embodiments for systems and methods that allow for a more accurate analyte concentration with a biosensor by obtaining two calibration codes, one for batch calibration due to manufacturing variations and the other for time calibration due to measured physical characteristics of the fluid sample.

7 Claims, 11 Drawing Sheets

ACCURATE ANALYTE MEASUREMENTS FOR ELECTROCHEMICAL TEST STRIP BASED ON MULTIPLE CALIBRATION PARAMETERS

PRIORITY

This application claims the benefits of priority under 35 USC § 119 from U.S. Provisional Patent Application Ser. No. 61/824,549, with an effective filing date under 35 USC § 100(i)(1)(B), for this application dated May 17, 2013, which prior provisional patent application is hereby incorporated by reference as if fully set forth herein this utility patent application.

BACKGROUND

Electrochemical glucose test strips, such as those used in the OneTouch® Ultra® whole blood testing kit, which is available from LifeScan, Inc., are designed to measure the concentration of glucose in a physiological fluid sample from patients with diabetes. The measurement of glucose can be based on the selective oxidation of glucose by the enzyme glucose oxidase (GO). The reactions that can occur in a glucose test strip are summarized below in Equations 1 and 2.

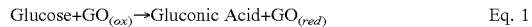

Glucose+GO$_{(ox)}$→Gluconic Acid+GO$_{(red)}$     Eq. 1

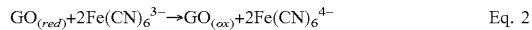

GO$_{(red)}$+2Fe(CN)$_6^{3-}$→GO$_{(ox)}$+2Fe(CN)$_6^{4-}$     Eq. 2

As illustrated in Equation 1, glucose is oxidized to gluconic acid by the oxidized form of glucose oxidase (GO$_{(ox)}$). It should be noted that GO$_{(ox)}$ may also be referred to as an "oxidized enzyme." During the reaction in Equation 1, the oxidized enzyme GO$_{(ox)}$ is converted to its reduced state, which is denoted as GO$_{(red)}$ (i.e., "reduced enzyme"). Next, the reduced enzyme GO$_{(red)}$ is re-oxidized back to GO$_{(ox)}$ by reaction with Fe(CN)$_6^{3-}$ the oxidized (referred to as either oxid mediator or ferricyanide) as illustrated in Equation 2. During the re-generation of GO$_{(red)}$ back to its oxidized state GO$_{(ox)}$, Fe(CN)$_6^{3-}$ is reduced to Fe(CN)$_6^{4-}$ (referred to as either reduced mediator or ferrocyanide).

When the reactions set forth above are conducted with a test signal in the form of potential applied between two electrodes, a test signal in the form of a current can be created by the electrochemical re-oxidation of the reduced mediator at the electrode surface. Thus, since, in an ideal environment, the amount of ferrocyanide created during the chemical reaction described above is directly proportional to the amount of glucose in the sample positioned between the electrodes, the test output signal generated would be proportional to the glucose content of the sample. A mediator, such as ferricyanide, is a compound that accepts electrons from an enzyme such as glucose oxidase and then donates the electrons to an electrode. As the concentration of glucose in the sample increases, the amount of reduced mediator formed also increases; hence, there is a direct relationship between the test output signal, resulting from the re-oxidation of reduced mediator, and glucose concentration. In particular, the transfer of electrons across the electrical interface results in the flow of a test output signal (2 moles of electrons for every mole of glucose that is oxidized). The test output signal resulting from the introduction of glucose can, therefore, be referred to as a glucose output signal.

The electrochemical biosensor noted above can be produced in enormous quantities, on the order of hundreds of millions and even billions of such biosensor per year. Production of a great number of batches of the same product lead inevitably to increased variation in the resulting product. This is driven by variation, among other factors of: manufacturing setting (production line); materials used; and volume throughput (stressing manufacturing ability). Generally, the task of good manufacturing practice is to limit the encountered variability by controlling all process and material parameters (settings, critical-to-quality factors, etc.) in line with the knowledge gained through a thorough characterization of the product and its manufacturability. However, no matter how good the operation side of the manufacture process is, a perfectly reproducible production line is never achievable. A balance is usually struck between the effort it takes to manufacture the product, yield achieved, the volume of product produced and the regulatory performance targets the product needs to satisfy. The finer the amount of control is exercised in manufacturing, the more expensive the overall product usually is.

One technique that others have used to deal with the variations in manufacturing is to accept a lower yield. For example, if there are wide variations on a yield of 90% of manufactured biosensors, the manufacturers could simply discard a large percentage (50% or more) of the biosensors that are outside acceptable manufacturing variations. This, however, results in waste and added cost due to the large number of discarded biosensors.

Another technique is to use calibration parameters, known as calibration slope and calibration intercept to those skilled in this field. Briefly, calibration curves can be generated by plotting measured glucose concentration against actual glucose concentration (or measured current versus YSI current), and a formula y=m*mx+c least squares fitted to the graph to give a value for batch slope m and batch intercept c for the remaining strips from the lot or batch. The graph can be divided into discrete areas and a code assigned to each area within the graph. The code itself is indexed to both the intercept and slope for a particular batch on which the calibration was performed thereon.

SUMMARY OF THE DISCLOSURE

With the recent invention of more accurate test measurement systems and methods described, shown and claimed in PCT/GB2012/053279, PCT/GB2012/053277, and PCT/GB2012/053276, with priority to U.S. Provisional Patent Application Ser. Nos. 61/581,087; 61/581,089; 61/581,099; and 61/581,100; and 61/654,013, applicant has devised a new technique to ensure tight conformance to referential datum for the new and more accurate test strip. In particular, applicant has devised a method that allows for a more accurate analyte concentration with a biosensor by usage of two calibration codes, one for batch calibration due to manufacturing variations and the other for time calibration due to measured physical characteristic of the fluid sample. The time calibration code allow for a more accurate determination of when to sample or measure a signal output from the biosensor while the calibration code ensures tight conformance to referential datum.

In a first aspect, applicant has devised a system for determining analyte concentration in a fluid. The system includes a biosensor and a processor. The biosensor has at least one electrode configured to receive an input signal that initiates an electrochemical reaction between a fluid sample and enzyme disposed on the at least one electrode. The processor is connected to a memory and a power supply to drive at least one input signal to the at least one electrode of the biosensor. In this system, the processor is configured to obtain a batch calibration code and a timing calibration code so that the processor determines, based on the timing calibration code, a particular time from a start of test measurement sequence at which to measure output signals from the sample and ascertains an analyte amount in the fluid sample from the output signals measured at the particular time and the batch calibration code.

In a second aspect, applicant has devised a system for determining analyte concentration in a fluid. The system includes a biosensor and a processor. The biosensor has at least one electrode configured to receive an input signal that initiates an electrochemical reaction between a fluid sample and enzyme disposed on the at least one electrode; the processor is connected to a memory and a power supply to drive at least one input signal to the at least one electrode of the biosensor, the processor configured to measure output signals proximate a particular time dictated by the timing calibration code and a nominal time from a start of the test measurement so that a glucose concentration in the fluid is calculated with the measured signal output proximate the particular time and the calibration code and the glucose concentration annunciated.

Further, applicants have devised a third aspect in analyte measurement technology to obtain glucose concentration from a biosensor having at least one electrode configured for connection with a glucose meter, the method can be achieved by: contacting a fluid sample with the at least one electrode to start a test measurement; obtaining a timing calibration code; calculating a particular time point ($t_c$) from the start of the test measurement for sampling a signal output of the sample based on the timing calibration code; applying a signal input to the sample; measuring a signal output from the sample from the start of a test measurement; determining at least one particular signal output proximate at least the particular time point after the start of the test measurement; obtaining a calibration code; calculating a glucose concentration from the at least one particular signal output and the calibration code.

In yet a fourth aspect, applicant has devised a method to determine a glucose concentration from a biosensor. The biosensor has at least one electrode configured to be connected to a signal source of a glucose meter. The method can be achieved by: obtaining a calibration code and a timing calibration code; applying an input signal to the sample to cause a physical transformation of the glucose in the sample and start a test measurement; measuring a signal output from the sample proximate a particular time dictated by the timing calibration code and a nominal time from a start of the test measurement; calculating a glucose concentration in the fluid with the signal output from the measuring step and the calibration code from the obtaining step; and annunciating the glucose concentration from the calculating step.

In a fifth aspect, applicant has devised a method to determine a glucose concentration from a biosensor. The biosensor has at least one electrode configured to be connected to a signal source of a glucose meter. The method can be achieved by: initiating a start of a test measurement sequence upon contact of a fluid sample to the at least one electrode; obtaining a timing multiplier coefficient (y1) and a timing additive coefficient (y2) for the biosensor; deriving a particular time point for measurement of signal output from the sample with the calibration multiplier coefficient and the calibration additive coefficient; obtaining a slope calibration (x1) and an intercept calibration (x2) for the biosensor; measuring a signal output from the sample from the start of the test measurement; determining at least one particular signal output proximate at least the particular time point after the start of the test measurement; calculating a glucose concentration from the at least one particular signal output, the slope calibration and the intercept calibration; and annunciating the glucose concentration from the calculating step.

In a sixth aspect, applicant has invented a method of determining an analyte concentration in a fluid with a biosensor. The biosensor is configured for measurement with an analyte meter. The method can be achieved by: driving a signal into the biosensor; starting a test sequence when an output signal is above a predetermined threshold; obtaining a batch calibration code specific to the biosensor and a timing calibration code specific to the biosensor; determining a particular time from the start of the test sequence to measure output signals from the biosensor based on information from the timing calibration code; measuring the output signals at the particular time; ascertaining the analyte amount in the fluid from the output signals measured at the particular time and the batch calibration code.

In an seventh aspect, applicant has provided for a system to determine analyte concentration in a fluid sample having an analyte to be determined. The system includes a biosensor and a meter. The biosensor has a batch calibration code and a timing calibration code stored in the biosensor. The meter is configured to obtain the calibration code and timing calibration code so that a measurement time for measuring output signals from the biosensor is obtained from the timing calibration code and a representation of the analyte in the sample is obtained from the batch calibration code and the output signals at the measurement.

And for these various aspects, the following features may also be utilized in various combinations with these previously disclosed aspects: the timing calibration code is correlated to a time multiplier value and an additive value; the calibration code is correlated to a slope of a particular batch of the biosensor and an intercept of a particular batch of the biosensor; the obtaining of the batch calibration code may include transmitting the batch calibration code from one of a storage container for the biosensor or the biosensor itself to a receiver of the glucose meter; the transmitting may include powering a RFID tag disposed in the biosensor for transmission of the batch calibration code to an RFID reader disposed in the glucose meter; the obtaining of the timing calibration code may include transmitting the timing calibration code from one of a storage container for the biosensor or the biosensor itself to the glucose meter; the transmitting may include powering an RFID tag disposed in the biosensor for transmission of the timing calibration code to an RFID reader disposed in the glucose meter; the obtaining may include transmitting the calibration multiplier coefficient and the calibration additive coefficient from one of a storage container for the biosensor or the biosensor itself to the glucose meter; the obtaining may include transmitting the slope calibration and intercept calibration from one of a storage container for the biosensor or the biosensor itself to the glucose meter.

In the aforementioned aspects of the disclosure, the steps of determining, estimating, calculating, computing, deriving and/or utilizing (possibly in conjunction with an equation) may be performed be an electronic circuit or a processor. These steps may also be implemented as executable instructions stored on a computer readable medium; the instructions, when executed by a computer may perform the steps of any one of the aforementioned methods.

In additional aspects of the disclosure, there are computer readable media, each medium comprising executable instructions, which, when executed by a computer, perform the steps of any one of the aforementioned methods.

In additional aspects of the disclosure, there are devices, such as test meters or analyte testing devices, each device or meter comprising an electronic circuit or processor configured to perform the steps of any one of the aforementioned methods.

These and other embodiments, features and advantages will become apparent to those skilled in the art when taken with reference to the following more detailed description of the exemplary embodiments of the invention in conjunction with the accompanying drawings that are first briefly described.

BRIEF DESCRIPTION OF THE DRAWINGS

The accompanying drawings, which are incorporated herein and constitute part of this specification, illustrate presently preferred embodiments of the invention, and, together with the general description given above and the detailed description given below, serve to explain features of the invention (wherein like numerals represent like elements), in which:

FIG. 3E illustrates a variation of the test strip of FIG. 3A in which one physical characteristic sensing electrode is disposed proximate the entrance and the other physical characteristic sensing electrode is at the terminal end of the test cell with the measurement electrodes disposed between the pair of physical characteristic sensing electrodes.

FIGS. 3C and 3D illustrate variations of FIG. 3A or 3B in which the physical characteristic sensing electrodes are disposed next to each other at the terminal end of the test chamber with the measurement electrodes upstream of the physical characteristic sensing electrodes.

MODES OF CARRYING OUT THE INVENTION

The following detailed description should be read with reference to the drawings, in which like elements in different drawings are identically numbered. The drawings, which are not necessarily to scale, depict selected embodiments and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

As used herein, the terms "about" or "approximately" for any numerical values or ranges indicate a suitable dimensional tolerance that allows the part or collection of components to function for its intended purpose as described herein. More specifically, "about" or "approximately" may refer to the range of values ±10% of the recited value, e.g., "about 90%" may refer to the range of values from 81% to 99%. In addition, as used herein, the terms "patient," "host," "user," and "subject" refer to any human or animal subject and are not intended to limit the systems or methods to human use, although use of the subject invention in a human patient represents a preferred embodiment. As used herein, "oscillating signal" includes voltage signal(s) or current signal(s) that, respectively, change polarity or alternate direction of the current or are multi-directional. Also used herein, the phrase "electrical signal" or "signal" is intended to include direct current signal, alternating signal or any signal within the electromagnetic spectrum. The terms "processor"; "microprocessor"; or "microcontroller" are intended to have the same meaning and are intended to be used interchangeably. As used herein, the term "annunciated" and variations on its root term indicate that an announcement may be provided via text, audio, visual or a combination of all modes or mediums of communication to a user. To inform the user of the qualitative aspect of the result, an indicia can be provided to indicate whether the result is outside of the desired range via a red indicia (or flashing message) or in-range by way of a green indicia or the like.

Figure 1:
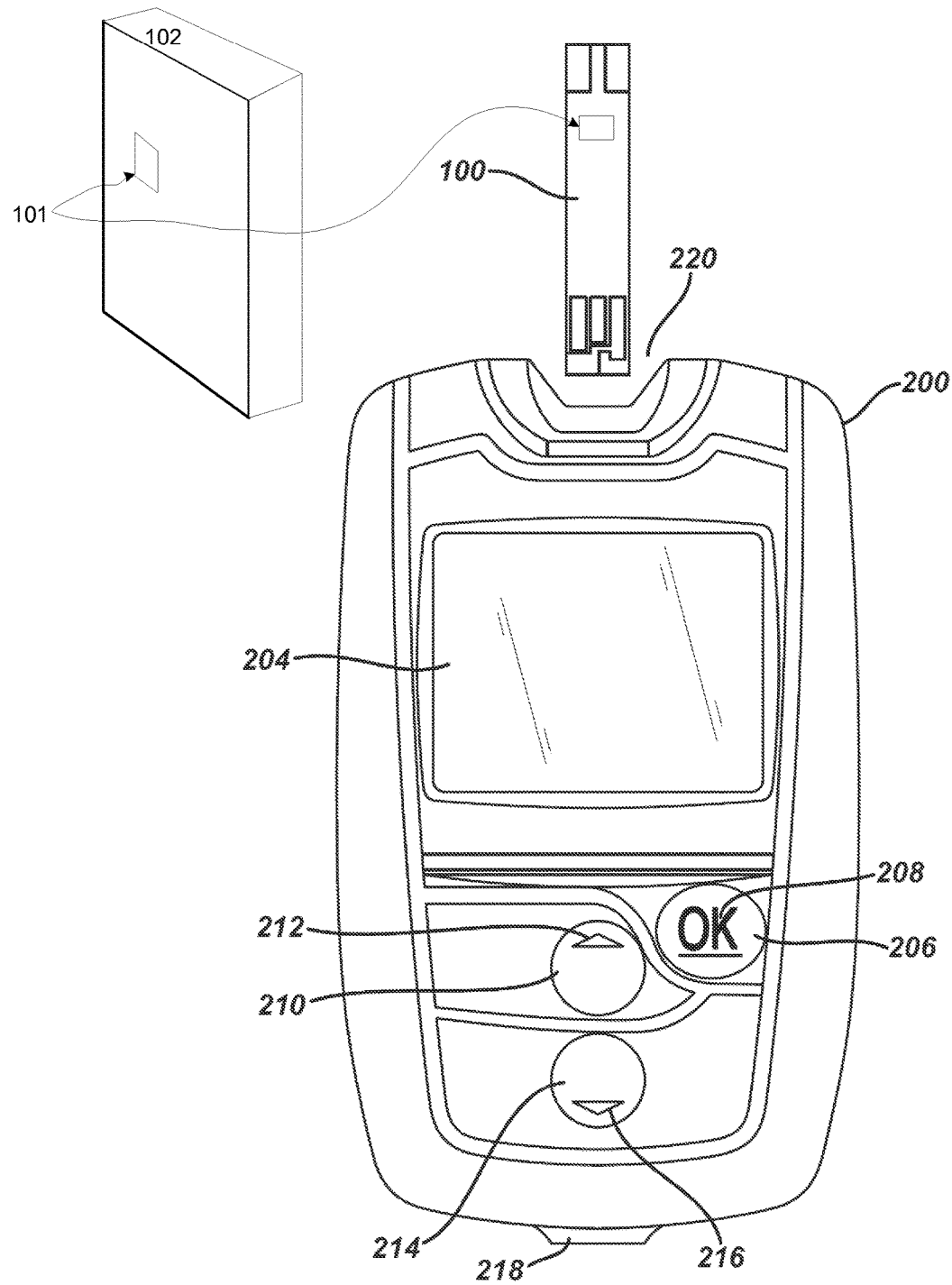
FIG. 1 illustrates an analyte measurement system with strip 100 and meter 200.

FIG. 1 illustrates a test meter 200, for testing analyte (e.g., glucose) levels in the blood of an individual with a test strip produced by the methods and techniques illustrated and described herein. Test meter 200 may include user interface inputs (206, 210, 214), which can be in the form of buttons, for entry of data, navigation of menus, and execution of commands. Data can include values representative of analyte concentration, and/or information that are related to the everyday lifestyle of an individual. Information, which is related to the everyday lifestyle, can include food intake, medication use, the occurrence of health check-ups, general health condition and exercise levels of an individual. Test meter 200 can also include a display 204 that can be used to report measured glucose levels, and to facilitate entry of lifestyle related information.

Test meter 200 may include a first user interface input 206, a second user interface input 210, and a third user interface input 214. User interface inputs 206, 210, and 214 facilitate entry and analysis of data stored in the testing device, enabling a user to navigate through the user interface displayed on display 204. User interface inputs 206, 210, and 214 include a first marking 208, a second marking 212, and a third marking 216, which help in correlating user interface inputs to characters on display 204.

Test meter 200 can be turned on by inserting a test strip 100 (or its variants in the Related Applications) into a strip port connector 220, by pressing and briefly holding first user interface input 206, or by the detection of data traffic across a data port 218. Test meter 200 can be switched off by removing test strip 100 (or its variants in the Related Applications), pressing and briefly holding first user interface input 206, navigating to and selecting a meter off option from a main menu screen, or by not pressing any buttons for a predetermined time. Display 204 can optionally include a backlight.

In one embodiment, test meter 200 can be configured to receive a calibration input for example, from any external source, when switching from a first test strip batch to a second test strip batch. Thus, in one exemplary embodiment, the meter is configured to receive a calibration input from external sources, such as a user interface (such as inputs 206, 210, 214), an inserted test strip, a separate code key, RFID tag, Near-Field-Communication tag, bar code, or a code strip to data port 218. The calibration input can be a set of values ascribed to a particular test strip batch. For example, the calibration input can include a batch slope and a batch intercept value for a particular test strip batch. The calibrations input, such as batch slope and batch intercept values, may be preset within the meter as will be described below.

Figure 2A:
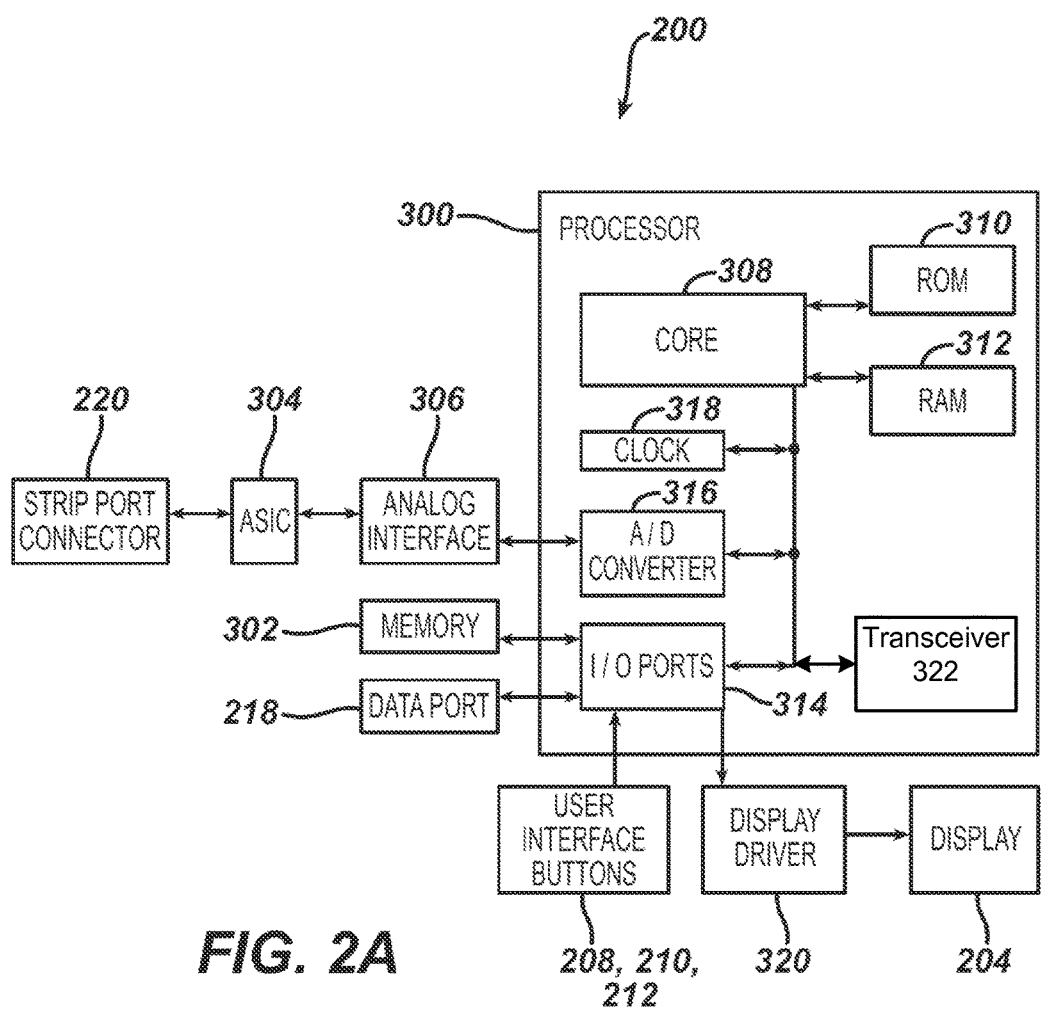
FIG. 2A illustrates in simplified schematic form the components of the meter 200.

Referring to FIG. 2A, an exemplary internal layout of test meter 200 is shown. Test meter 200 may include a processor 300, which in some embodiments described and illustrated herein is a 32-bit RISC microcontroller. In the preferred embodiments described and illustrated herein, processor 300 is preferably selected from the MSP 430 family of ultra-low power microcontrollers manufactured by Texas Instruments of Dallas, Tex. The processor can be bi-directionally connected via I/O ports 314 to a memory 302, which in some embodiments described and illustrated herein is an EEPROM. Also connected to processor 300 via I/O ports 314 are the data port 218, the user interface inputs 206, 210, and 214, and a display driver 320. Data port 218 can be connected to processor 300, thereby enabling transfer of data between memory 302 and an external device, such as a personal computer. A suitable wireless transceiver 322 is provided in the meter to enable the meter to read calibration code and timing code stored in readable memory tag affixed to the biosensor or vial such as, for example, a radio-frequency-identification tag or RFID tag 101 (FIG. 1). Examples of RFID are known in the field such as, for example, EP1825806; U.S. Pat. No. 8,390,455; 8,358,210; or 8,410,939, all of which are incorporated by reference in their entireties herein this application.

In one embodiment, the user interface inputs 206, 210, and 214 are directly connected to processor 300. Processor 300 controls display 204 via display driver 320. Memory 302 may be pre-loaded with calibration information, such as batch slope and batch intercept values correlated to calibration code, during production of test meter 200. This pre-loaded calibration information can be accessed and used by processor 300 upon receiving a suitable signal (such as current) from the strip via strip port connector 220 so as to calculate a corresponding analyte level (such as blood glucose concentration) using the signal and the calibration information without receiving calibration input from any external source.

In embodiments described and illustrated herein, test meter 200 may include an Application Specific Integrated Circuit (ASIC) 304, so as to provide electronic circuitry used in measurements of glucose level in blood that has been applied to a test strip 100 (or its variants in the Related Applications) inserted into strip port connector 220. Analog voltages can pass to and from ASIC 304 by way of an analog interface 306. Analog signals from analog interface 306 can be converted to digital signals by an A/D converter 316. Processor 300 further includes a core 308, a ROM 310 (containing computer code), a RAM 312, and a clock 318. In one embodiment, the processor 300 is configured (or programmed) to disable all of the user interface inputs except for a single input upon a display of an analyte value by the display unit such as, for example, during a time period after an analyte measurement. In an alternative embodiment, the processor 300 is configured (or programmed) to ignore any input from all of the user interface inputs except for a single input upon a display of an analyte value by the display unit. Detailed descriptions and illustrations of the meter 200 are shown and described in International Patent Application Publication No. WO2006040200, which is hereby incorporated by reference into this application as if fully set forth herein.

Figure 3A:
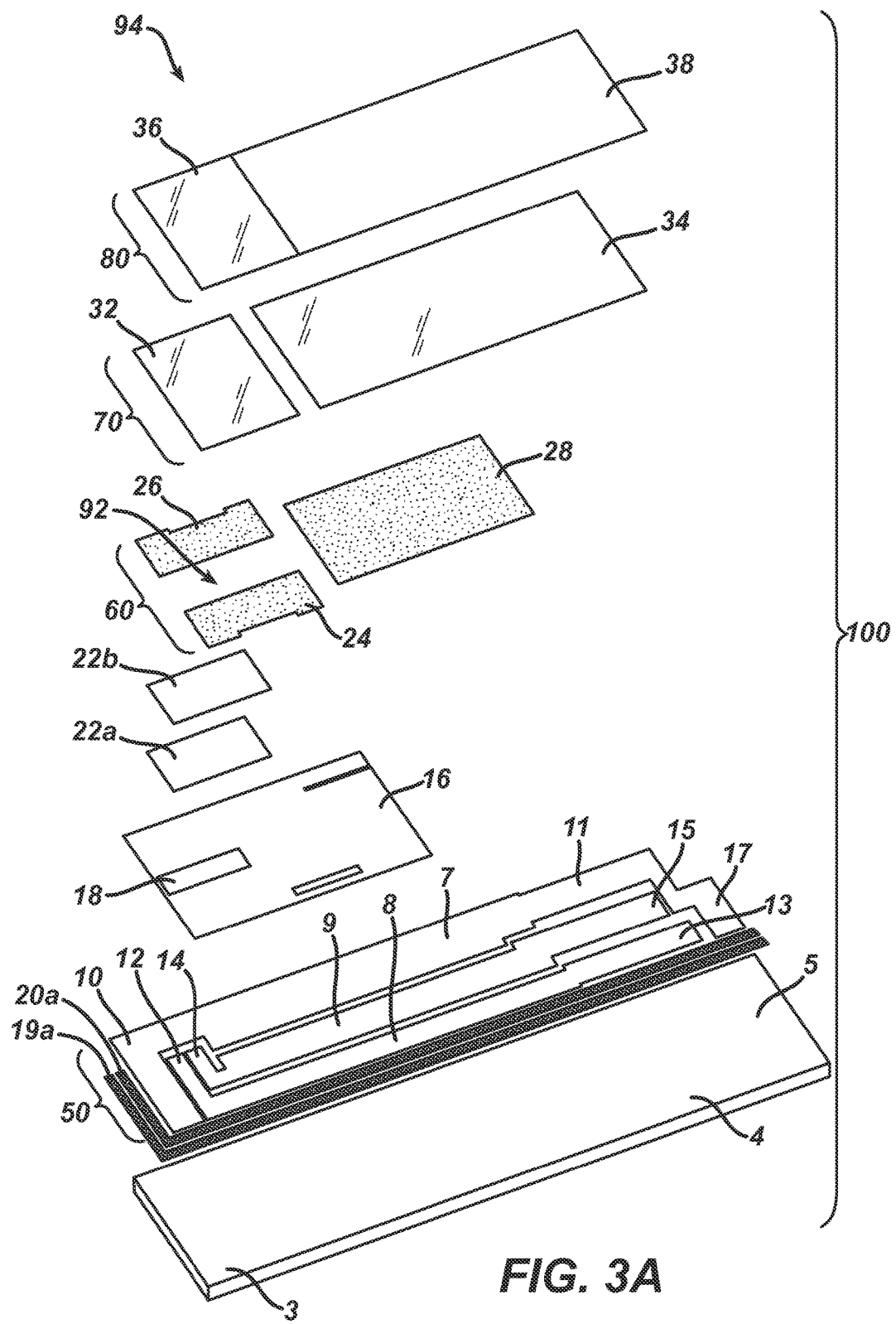
FIG. 3A illustrates the test strip 100 of the system of FIG. 1 in which there are two physical characteristic sensing electrodes upstream of the measurement electrodes.

FIG. 3A is an exemplary exploded perspective view of a test strip 100, which may include seven layers disposed on a substrate 5. The seven layers disposed on substrate 5 can be a first conductive layer 50 (which can also be referred to as electrode layer 50), an insulation layer 16, two overlapping reagent layers 22a and 22b, an adhesive layer 60 which includes adhesive portions 24, 26, and 28, a hydrophilic layer 70, and a top layer 80 which forms a cover 94 for the test strip 100. Test strip 100 may be manufactured in a series of steps where the conductive layer 50, insulation layer 16, reagent layers 22, and adhesive layer 60 are sequentially deposited on substrate 5 using, for example, a screen-printing process. Note that the electrodes 10, 12, and 14) are disposed for contact with the reagent layer 22a and 22b whereas the physical characteristic sensing electrodes 19a and 20a are spaced apart and not in contact with the reagent layer 22. Hydrophilic layer 70 and top layer 80 can be disposed from a roll stock and laminated onto substrate 5 as either an integrated laminate or as separate layers. Test strip 100 has a distal portion 3 and a proximal portion 4 as shown in FIG. 3A.

Figure 3B:
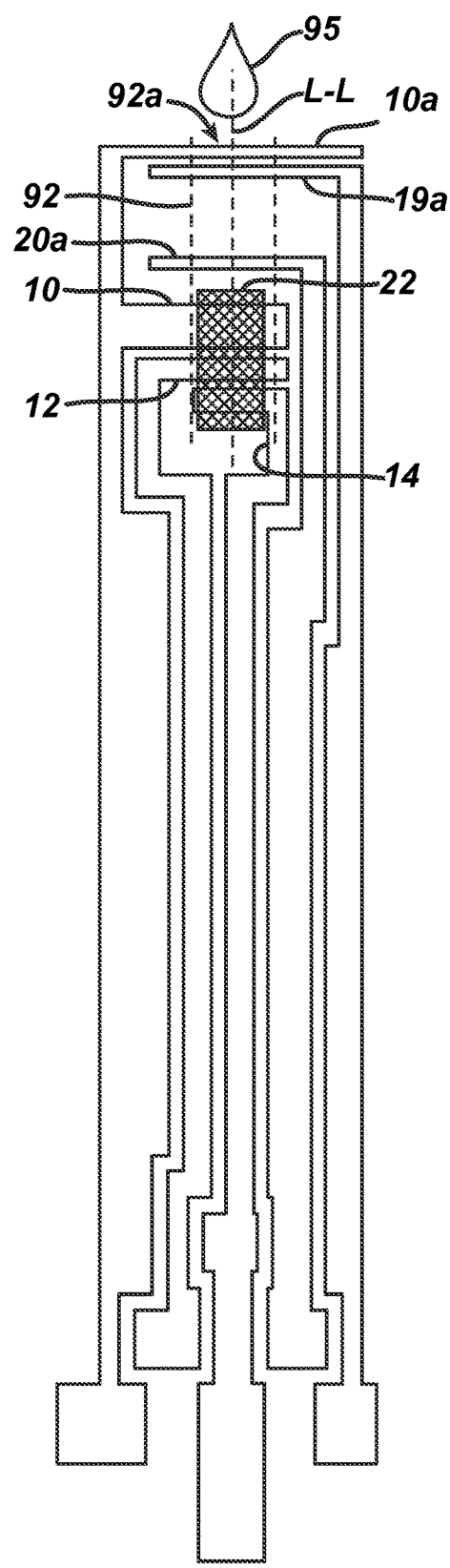
FIG. 3B illustrates a variation of the test strip of FIG. 3A in which a shielding or grounding electrode is provided for proximate the entrance of the test chamber.

Test strip 100 may include a sample-receiving chamber 92 through which a physiological fluid sample 95 may be drawn through or deposited (FIG. 3B). The physiological fluid sample discussed herein may be blood. Sample-receiving chamber 92 can include an inlet at a proximal end and an outlet at the side edges of test strip 100, as illustrated in FIG. 3A. A fluid sample 95 can be applied to the inlet along axis L-L (FIG. 3B) to fill a sample-receiving chamber 92 so that glucose can be measured. The side edges of a first adhesive pad 24 and a second adhesive pad 26 located adjacent to reagent layer 22 each define a wall of sample-receiving chamber 92, as illustrated in FIG. 3A. A bottom portion or "floor" of sample-receiving chamber 92 may include a portion of substrate 5, conductive layer 50, and insulation layer 16, as illustrated in FIG. 3A. A top portion or "roof" of sample-receiving chamber 92 may include distal hydrophilic portion 32, as illustrated in FIG. 3A. For test strip 100, as illustrated in FIG. 3A, substrate 5 can be used as a foundation for helping support subsequently applied layers. Substrate 5 can be in the form of a polyester sheet such as a polyethylene tetraphthalate (PET) material (Hostaphan PET supplied by Mitsubishi). Substrate 5 can be in a roll format, nominally 350 microns thick by 370 millimeters wide and approximately 60 meters in length.

A conductive layer is required for forming electrodes that can be used for the electrochemical measurement of glucose. First conductive layer 50 can be made from a carbon ink that is screen-printed onto substrate 5. In a screen-printing process, carbon ink is loaded onto a screen and then transferred through the screen using a squeegee. The printed carbon ink can be dried using hot air at about 140° C. The carbon ink can include VAGH resin, carbon black, graphite (KS 15), and one or more solvents for the resin, carbon and graphite mixture. More particularly, the carbon ink may incorporate a ratio of carbon black:VAGH resin of about 2.90:1 and a ratio of graphite:carbon black of about 2.62:1 in the carbon ink.

For test strip 100, as illustrated in FIG. 3A, first conductive layer 50 may include a reference electrode 10, a first working electrode 12, a second working electrode 14, third and fourth physical characteristic sensing electrodes 19a and 19b, a first contact pad 13, a second contact pad 15, a reference contact pad 11, a first working electrode track 8, a second working electrode track 9, a reference electrode track 7, and a strip detection bar 17. The physical characteristic sensing electrodes 19a and 20a are provided with respective electrode tracks 19b and 20b. The conductive layer may be formed from carbon ink. First contact pad 13, second contact pad 15, and reference contact pad 11 may be adapted to electrically connect to a test meter. First working electrode track 8 provides an electrically continuous pathway from first working electrode 12 to first contact pad 13. Similarly, second working electrode track 9 provides an electrically continuous pathway from second working electrode 14 to second contact pad 15. Similarly, reference electrode track 7 provides an electrically continuous pathway from reference electrode 10 to reference contact pad 11. Strip detection bar 17 is electrically connected to reference contact pad 11. Third and fourth electrode tracks 19b and 20b connect to the respective electrodes 19a and 20a. A test meter can detect that test strip 100 has been properly inserted by measuring a continuity between reference contact pad 11 and strip detection bar 17, as illustrated in FIG. 3A.

Variations of the test strip 100 are shown in applicant's related application Ser. Nos. 61/581,087; 61/581,089; 61/581,099; and 61/581,100, all filed on the same day of Dec. 29, 2011, U.S. Provisional Patent Application Ser. No. 61/654,013, filed on May 31, 2012; and International Patent Application PCT/GB2012/053279, PCT/GB2012/053277, and PCT/GB2012/053276, filed Dec. 28, 2012, (hereafter "Related Applications"). It is the intention of applicant that the scope of the invention claimed herein is also applicable but not limited to the variety of strips described in these prior filed Related Applications.

In the embodiment of FIG. 3B which is a variation of the test strip of FIG. 3A, an additional electrode 10a is provided as an extension of any of the plurality of electrodes 19a, 20a, 14, 12, and 10. It must be noted that the built-in shielding or grounding electrode 10a is used to reduce or eliminate any capacitance coupling between the finger or body of the user and the characteristic measurement electrodes 19a and 20a. The grounding electrode 10a allows for any capacitance to be directed away from the sensing electrodes 19a and 20a. To do this, the grounding electrode 10a can be connected any one of the other five electrodes or to its own separate contact pad (and track) for connection to ground on the meter instead of one or more of contact pads 15, 17, 13 via respective tracks 7, 8, and 9. In a preferred embodiment, the grounding electrode 10a is connected to one of the three electrodes that has reagent 22 disposed thereon. In a most preferred embodiment, the grounding electrode 10a is connected to electrode 10. Being the grounding electrode, it is advantageous to connect the grounding electrode to the reference electrode (10) so as not to contribute any additional current to the working electrode measurements which may come from background interfering compounds in the sample. Further by connecting the shield or grounding electrode 10a to electrode 10 this is believed to effectively increase the size of the counter electrode 10 which can become limiting especially at high signals. In the embodiment of FIG. 3B, the reagent is arranged so that they are not in contact with the measurement electrodes 19a and 20a. Alternatively, in the embodiment of FIG. 3C, the reagent 22 is arranged so that the reagent 22 contacts at least one of the sensing electrodes 19a and 20a.

Figure 3C:
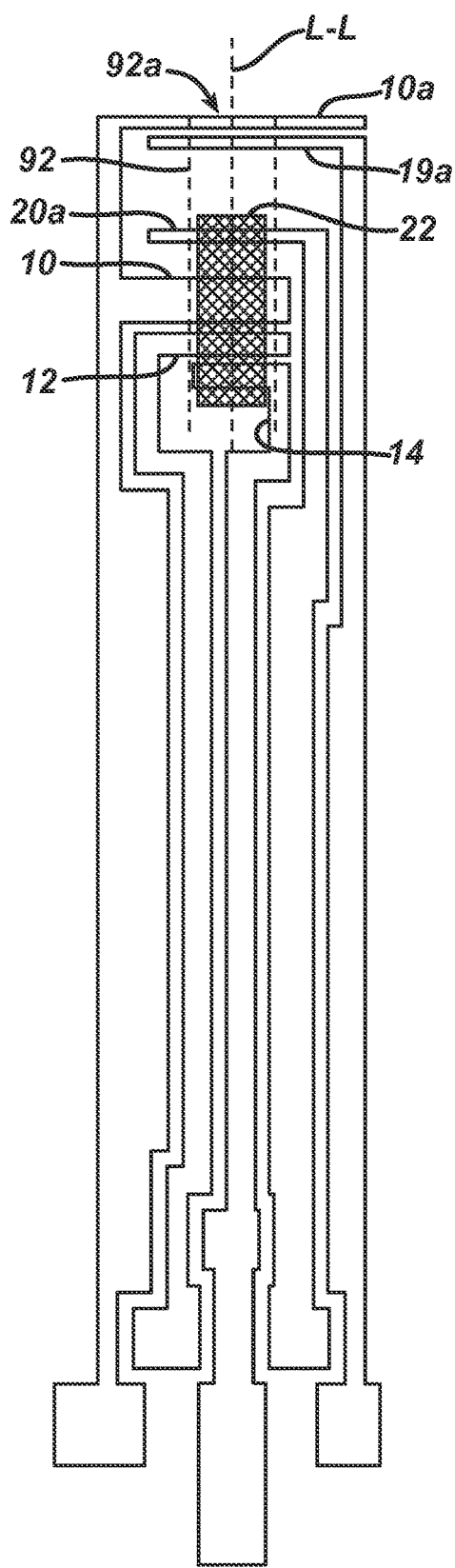
FIG. 3C illustrates a variation of the test strip of FIG. 3B in which a reagent area has been extended upstream to cover at least one of the physical characteristic sensing electrodes.
Figure 3D:
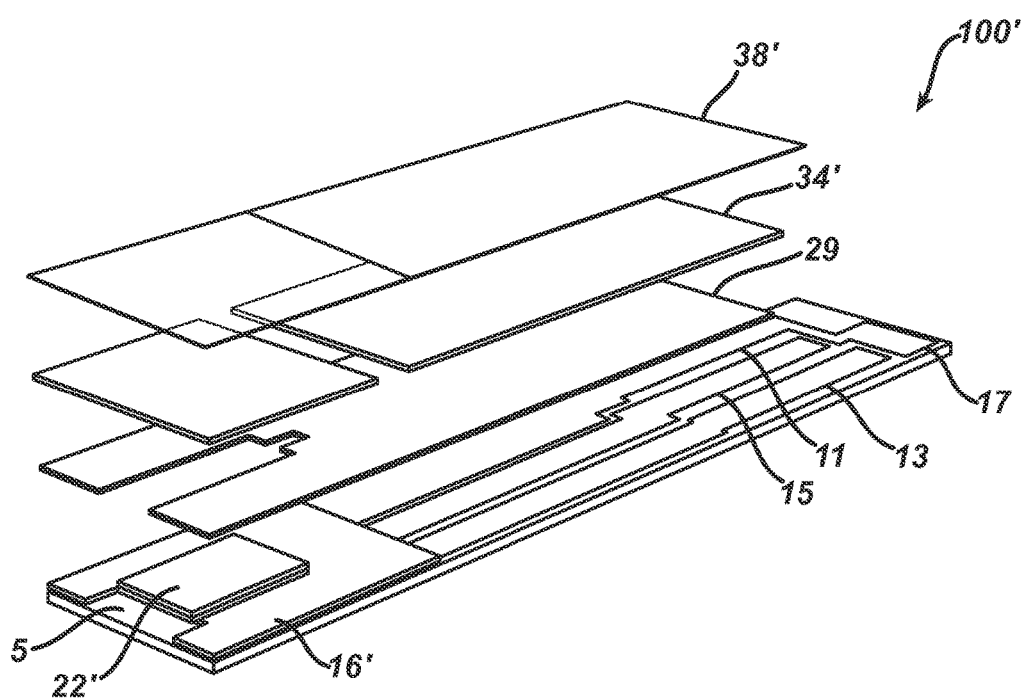
FIG. 3D illustrates a variation of test strip 100 of FIGS. 3A, 3B and 3C in which certain components of the test strip have been integrated together into a single unit.

In an alternate version of test strip 100, shown here in FIG. 3D, the top layer 38, hydrophilic film layer 34 and spacer 29 have been combined together to form an integrated assembly for mounting to the substrate 5 with reagent layer 22' disposed proximate insulation layer 16'.

In the embodiment of FIG. 3B, the analyte measurement electrodes 10, 12, and 14 are disposed in generally the same configuration as in FIG. 3A, 3C, or electrodes 11, 13, and 15 in FIG. 3D. Alternatively, the electrodes to sense physical characteristic (e.g., hematocrit) level, can be disposed in a spaced apart configuration in which one electrode 19a is proximate an entrance 92a to the test chamber 92 and another electrode 20a is at the opposite end of the test chamber 92 (shown in FIG. 3B of the Related Applications) or both sensing electrodes being distal from the entrance 92a (shown in FIGS. 3C and 3D of the Related Applications). At least one of the electrodes on the biosensor is disposed to be in contact with a reagent layer 22.

In FIGS. 3C and 3D, the physical characteristic (e.g., hematocrit) sensing electrodes 19a and 20a are disposed adjacent each other and may be placed at the opposite end of the entrance 92a to the test chamber 92 adjacent and downstream of electrode 14 along axis L-L or adjacent the entrance 92a (FIGS. 3A-3D). In all of these embodiments, the physical characteristic sensing electrodes are spaced apart from the reagent layer 22 so that these physical characteristic sensing electrodes are not impacted by the electrochemical reaction of the reagent in the presence of a fluid sample (e.g., blood or interstitial fluid) containing glucose.

As is known, conventional electrochemical-based analyte test strips employ a working electrode along with an associated counter/reference electrode and enzymatic reagent layer to facilitate an electrochemical reaction with an analyte of interest and, thereby, determine the presence and/or concentration of that analyte. For example, an electrochemical-based analyte test strip for the determination of glucose concentration in a fluid sample can employ an enzymatic reagent that includes the enzyme glucose oxidase and the mediator ferricyanide (which is reduced to the mediator ferrocyanide during the electrochemical reaction). Such conventional analyte test strips and enzymatic reagent layers are described in, for example, U.S. Pat. Nos. 5,708,247; 5,951,836; 6,241,862; and 6,284,125; each of which is hereby incorporated by reference herein to this application. In this regard, the reagent layer employed in various embodiments provided herein can include any suitable sample-soluble enzymatic reagents, with the selection of enzymatic reagents being dependent on the analyte to be determined and the bodily fluid sample. For example, if glucose is to be determined in a fluid sample, enzymatic reagent layer 22 can include glucose oxidase or glucose dehydrogenase along with other components necessary for functional operation.

In general, enzymatic reagent layer 22 includes at least an enzyme and a mediator. Examples of suitable mediators include, for example, ruthenium, Hexaammine Ruthenium (III) Chloride, ferricyanide, ferrocene, ferrocene derivatives, osmium bipyridyl complexes, and quinone derivatives. Examples of suitable enzymes include glucose oxidase, glucose dehydrogenase (GDH) using a pyrroloquinoline quinone (PQQ) co-factor, GDH using a nicotinamide adenine dinucleotide (NAD) co-factor, and GDH using a flavin adenine dinucleotide (FAD) co-factor. Enzymatic reagent layer 22 can be applied during manufacturing using any suitable technique including, for example, screen printing.

Applicant note that enzymatic reagent layer may also contain suitable buffers (such as, for example, Tris HCl, Citraconate, Citrate and Phosphate), hydroxyethylcelulose [HEC], carboxymethylcellulose, ethycellulose and alginate, enzyme stabilizers and other additives as are known in the field.

Further details regarding the use of electrodes and enzymatic reagent layers for the determination of the concentrations of analytes in a bodily fluid sample, albeit in the absence of the phase-shift measurement electrodes, analytical test strips and related methods described herein, are in U.S. Pat. No. 6,733,655, which is hereby fully incorporated by reference herein to this application.

In the various embodiments of the test strip, there are two measurements that are made to a fluid sample deposited on the test strip. One measurement is that of the concentration of the analyte (e.g. glucose) in the fluid sample while the other is that of physical characteristic (e.g., hematocrit) in the same sample. The measurement of the physical characteristic (e.g., hematocrit) is used to modify or correct the glucose measurement so as to remove or reduce the effect of red blood cells on the glucose measurements. Both measurements (glucose and hematocrit) can be performed in sequence, simultaneously or overlapping in duration. For example, the glucose measurement can be performed first then the physical characteristic (e.g., hematocrit); the physical characteristic (e.g., hematocrit) measurement first then the glucose measurement; both measurements at the same time; or a duration of one measurement may overlap a duration of the other measurement. Each measurement is discussed in detail as follows with respect to FIGS. 4A and 4B.

Figure 4A:
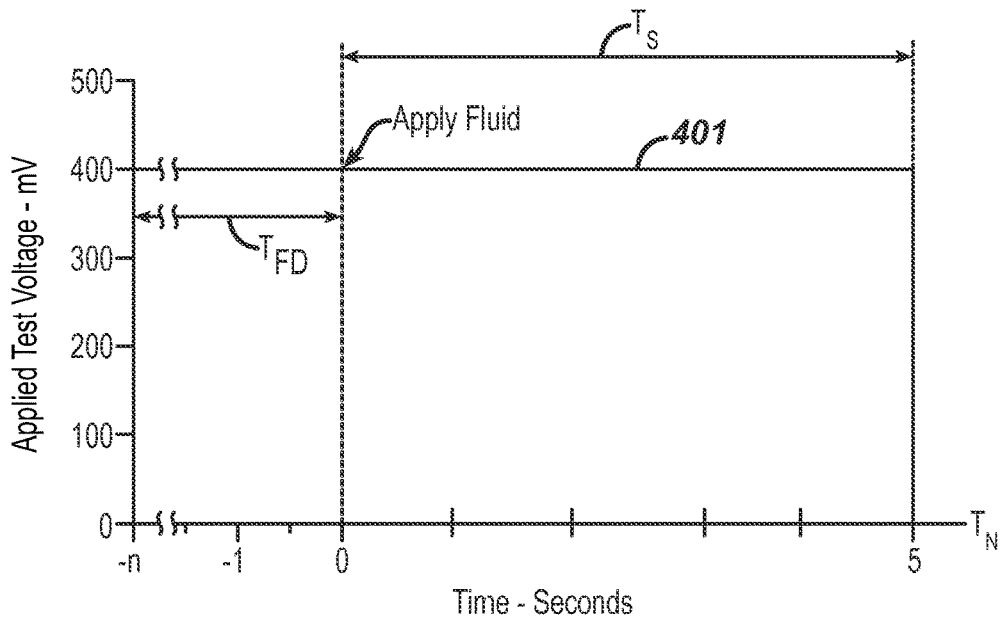
FIG. 4A illustrates a graph of time over applied potential to the test strip of FIG. 1.

FIG. 4A is an exemplary chart of a test signal applied to test strip 100 and its variations shown here in FIGS. 3A-3D. Before a fluid sample is applied to test strip 100 (or its variants in the Related Applications), test meter 200 is in a fluid detection mode in which a first test signal of about 400 millivolts is applied between second working electrode and reference electrode. A second test signal 401 of about 400 millivolts is preferably applied simultaneously between first working electrode (e.g., electrode 12 of strip 100) and reference electrode (e.g., electrode 10 of strip 100). Alternatively, the second test signal may also be applied contemporaneously such that a time interval of the application of the first test signal overlaps with a time interval in the application of the second test voltage. The test meter may be in a fluid detection mode during fluid detection time interval $T_{FD}$ prior to the detection of physiological fluid at starting time at zero. In the fluid detection mode, test meter 200 determines when a fluid is applied to test strip 100 (or its variants in the Related Applications) such that the fluid wets either first working electrode 12 or second working electrode 14 and reference electrode 10. Once test meter 200 recognizes that the physiological fluid has been applied because of, for example, a sufficient increase in the measured test current at either the first working electrode 12 or second working electrode 14 (or both electrodes) with respect to the reference electrode 10, test meter 200 assigns a zero second marker at zero time "0" and starts the test sequence time interval $T_S$. Test meter 200 may sample the current transient output at a suitable sampling rate, such as, for example, every 1 milliseconds to every 100 milliseconds. Upon the completion of the test time interval $T_S$, the test signal is removed. For simplicity, FIG. 4A only shows the first test signal 401 applied to test strip 100 (or its variants in the Related Applications).

Hereafter, a description of how glucose concentration is determined from the known current transients (e.g., the measured electrical current response in nanoamperes as a function of time) that are measured when the test voltages of FIG. 4A are applied to the test strip 100 (or its variants in the Related Applications).

Figure 4B:
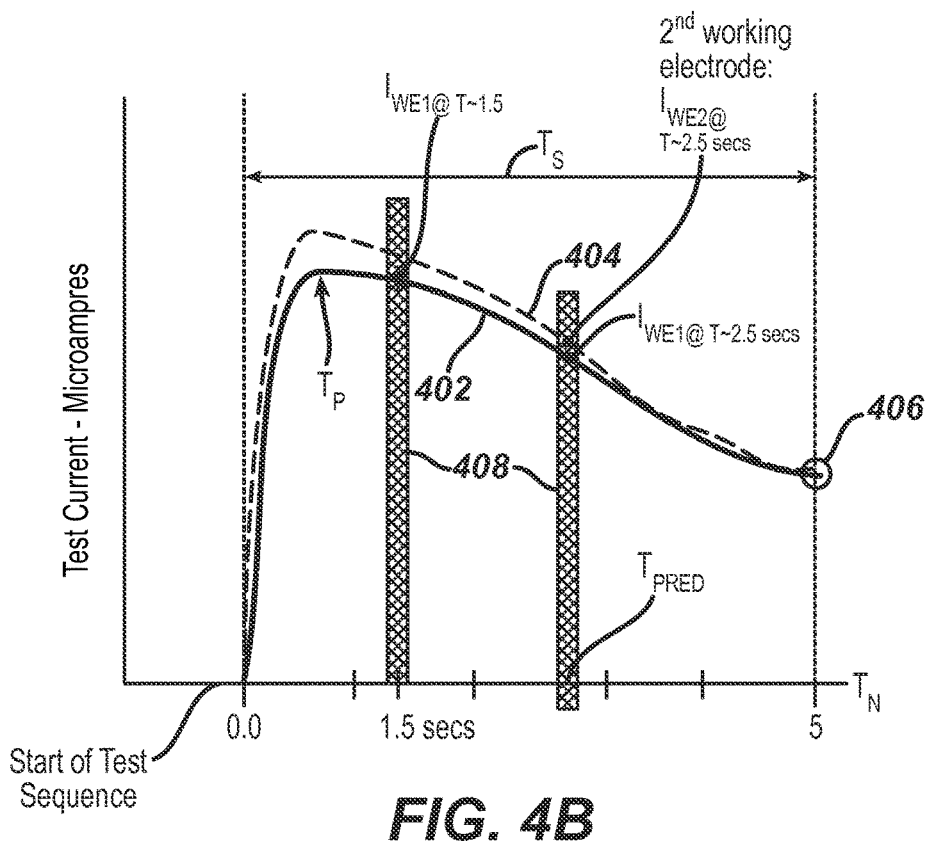
FIG. 4B illustrates a graph of time over output signal from the test strip of FIG. 1.

In FIG. 4A, the first and second test voltages applied to test strip 100 (or its variants in the Related Applications) are generally from about +100 millivolts to about +600 millivolts. In one embodiment in which the electrodes include carbon ink and the mediator includes ferricyanide, the test signal is about +400 millivolts. Other mediator and electrode material combinations will require different test voltages, as is known to those skilled in the art. The duration of the test voltages is generally from about 1 to about 5 seconds after a reaction period and is typically about 3 seconds after a reaction period. Typically, test sequence time $T_S$ is measured relative to time $t_0$. As the voltage 401 is maintained in FIG. 4A for the duration of $T_S$, output signals are generated, shown here in FIG. 4B with the current transient 402 for the first working electrode 12 being generated starting at zero time and likewise the current transient 404 for the second working electrode 14 is also generated with respect to the zero time. It is noted that while the signal transients 402 and 404 have been placed on the same referential zero point for purposes of explaining the process, in physical terms, there is a slight time differential between the two signals due to fluid flow in the chamber towards each of the working electrodes 12 and 14 along axis L-L. However, the current transients are sampled and configured in the microcontroller to have the same start time. In FIG. 4B, the current transients build up to a peak proximate peak time Tp at which time, the current slowly drops off until approximately one of 2.5 seconds or 5 seconds after zero time. At the point 406, approximately at 5 seconds, the output signal for each of the working electrodes 12 and 14 may be measured and added together. Alternatively, the signal from only one of the working electrodes 12 and 14 can be doubled. From knowledge of the parameters of the test strip (e.g., batch calibration code offset and batch $z_1$) for the particular test strip 100 and its variations, the analyte (e.g., glucose) concentration can be calculated. Output transient 402 and 404 can be sampled to derive signals $I_E$ (by summation of each of the current $I_{WE1}$ and $I_{WE2}$ or doubling of one of $I_{WE1}$ or $I_{WE2}$) at various time positions during the test sequence.

It is noted that "batch intercept" (or "$z_2$") and "batch slope" (or "$z_1$") are the parametric values of the biosensor obtained by measuring calibration data from a lot or batch of test strips. Batch slope as a calibration parameter is well understood by those skilled in the art as referring to an amount of electrical signal produced by a predetermined amount (unit) of the measured analyte. Similarly, batch intercept is also well understood by those skilled in the art as a value determined from a linear regression of a plot of biosensor output signal versus a reference glucose concentration. To determine the batch slope and intercepts, around 1500 strips are typically selected at random from the lot or batch. Physiological fluid (e.g., blood) from donors is spiked to various analyte levels, typically six different glucose concentrations. Typically, blood from 12 different donors is spiked to each of the six levels. Eight strips are given blood from identical donors and levels so that a total of 12×6× 8=576 tests are conducted for that lot. These are benchmarked against actual analyte level (e.g., blood glucose concentration) by measuring these using a standard laboratory analyzer such as Yellow Springs Instrument (YSI). A graph of measured glucose concentration is plotted against actual glucose concentration (or measured current versus YSI current) and a formula y=mx+c least squares fitted to the graph to give a value for batch slope of "m" and batch intercept "c" for the remaining strips from the lot or batch. The applicant has also provided methods and systems in which the batch slope is derived during the determination of an analyte concentration. The "batch slope" (or "$z_1$"), may therefore be defined as the measured or derived gradient of the line of best fit for a graph of measured glucose concentration plotted against actual glucose concentration (or measured current versus YSI current). The "batch intercept" (or "$z_2$"), may therefore be defined as the point at which the line of best fit for a graph of measured glucose concentration plotted against actual glucose concentration (or measured current versus YSI current) meets the y axis.

It is worthwhile here to note that the various components, systems and procedures described earlier allow for applicant to provide an analyte measurement system that heretofore was not available in the art. In particular, this system includes a test strip that has a substrate and a plurality of electrodes connected to respective electrode connectors. The system further includes an analyte meter 200 that has a housing, a test strip port connector configured to connect to the respective electrode connectors of the test strip, and a microcontroller 300, shown here in FIG. 2B. The microprocessor 300 is in electrical communication with the test strip port connector 220 to apply electrical signals or sense electrical signals from the plurality of electrodes.

Figure 2B:
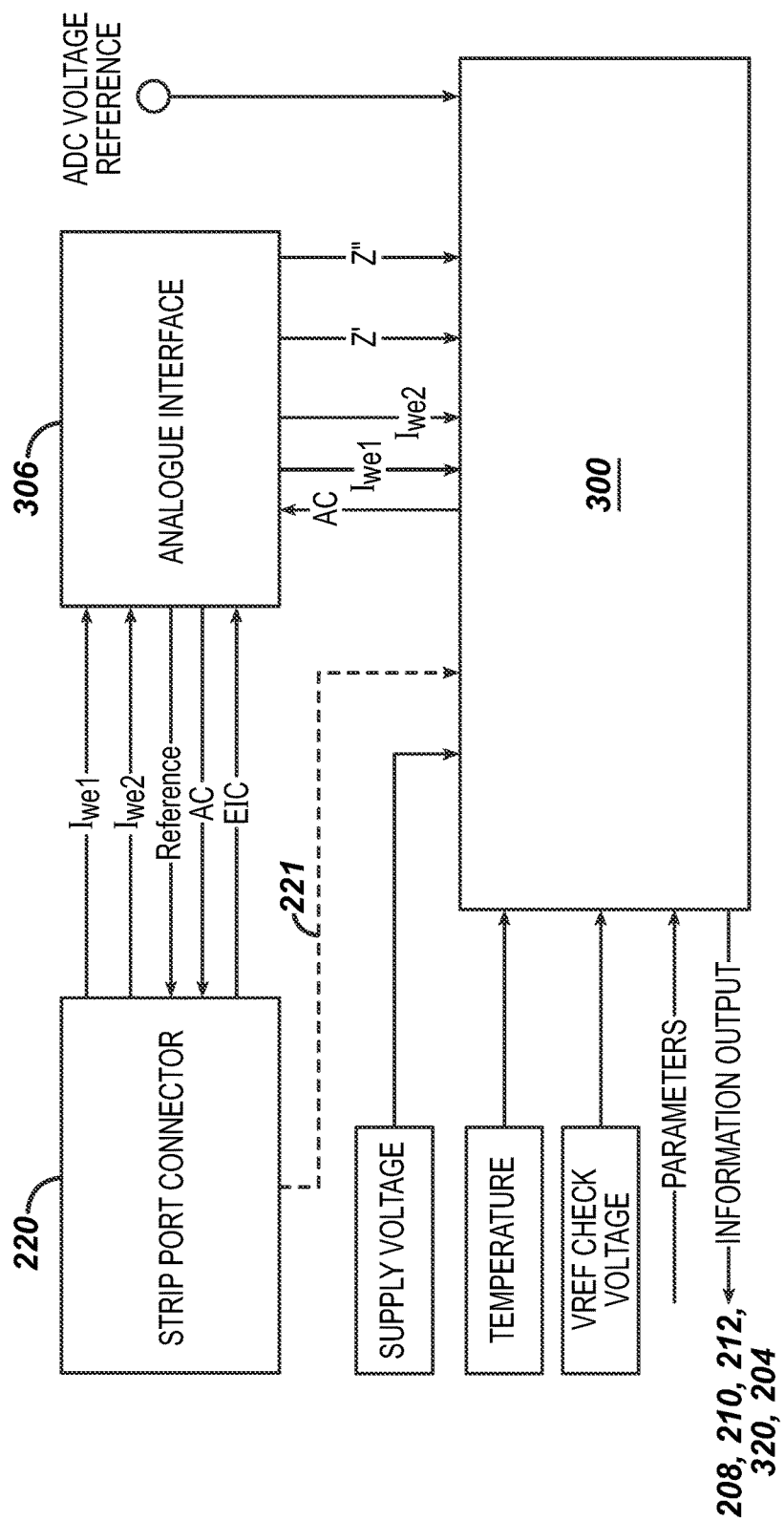
FIG. 2B illustrates in simplified schematic a preferred implementation of a variation of meter 200.

Referring back to FIG. 2B, details of a preferred implementation of meter 200 where the same numerals in FIGS. 2A and 2B have a common description. In FIG. 2B, a strip port connector 220 is connected to the analogue interface 306 by five lines including an impedance sensing line EIC to receive signals from physical characteristic sensing electrode(s), alternating signal line AC driving signals to the physical characteristic sensing electrode(s), reference line for a reference electrode, and current sensing lines from respective working electrode 1 and working electrode 2. A strip detection line 221 can also be provided for the connector 220 to indicate insertion of a test strip. The analog interface 306 provides four inputs to the processor 300: (1) real impedance Z'; (2) imaginary impedance Z"; (3) output signal sampled or measured from working electrode 1 of the biosensor or $I_{we1}$; (4) output signal sampled or measured from working electrode 2 of the biosensor or $I_{we2}$. There is one output from the processor 300 to the interface 306 to drive an oscillating signal AC of any value from 25 kHz to about 250 kHz or higher to the physical characteristic sensing electrodes. A phase differential P (in degrees) can be determined from the real impedance Z' and imaginary impedance Z". Details of the impedance sensing technique to derive the physical characteristic of the fluid sample can be gleaned from PCT/GB2012/053279, PCT/GB2012/053277, and PCT/GB2012/053276, with priority to U.S. Provisional Patent Application Ser. Nos. 61/581,087; 61/581,089; 61/581,099; and 61/581,100; and 61/654,013, all of these patent applications are hereby incorporated by reference into this application as if fully set forth herein.

Glucose concentration $G_0$ can be thereafter be determined from Equation 3 as follows:

$$G_0=[I_E-z_2] \div z_1 \qquad \text{Eq. 3}$$

where $I_E$ is a signal (e.g., current proportional to analyte concentration) which could be the total current from all of the electrodes in the biosensor (e.g., from all five electrodes in sensor 100, both working electrodes 12 and 14 (where $I_E=I_{we1}+I_{we2}$ or $I_E=2*((I_{we1}+I_{we2})/2)$) or alternatively from one of the working electrodes where $I_E=2*I_{we1}$, or $I_E=2*I_{we2}$;

$I_{we1}$ is the signal (e.g., current) measured for the first working electrode at the set sampling time;

$I_{we2}$ is the signal (e.g., current) measured for the second working electrode at the set sampling time;

$z_1$ is the value obtained from calibration testing of a batch of test strips of which this particular strip comes from;

$z_2$ is the value obtained from calibration testing of a batch of test strips of which this particular strip comes from.

The variables $z_1$ and $z_2$ can be correlated together during calibration post-manufacturing such that a single code can be used to represent the relevant slope (i.e., $z_1$) and intercept (i.e., $z_2$). That is, a single code can be used to correlate the two calibration parameters and multiple codes can be used to represent corresponding pairs of calibration parameters. For example, Table 1 illustrates that each of the 36 codes correlates to the relevant slope and intercept parameters to ensure that a batch of biosensors are calibrated to standardized biosensor glucose measurement response. Although the codes (1-36) are numeric, they can also be represented as alphabetized codes or even alphanumeric. At the point of batch release testing information is gathered about the appropriate setting for $z_1$ and $z_2$ values and a batch calibration code is assigned (see Table 1). This information is locked in the biosensor or vial 102 with a suitable means such as, for example RFID, bar coding, or NFC, before packaging and batch release.

TABLE 1

Glucose Calibration Code
BATCH CALIBRATION CODES

| | Slope: $z_1$ | | | | | |
|---|---|---|---|---|---|---|
| Intercept: $z_2$ | 8.5 nA/ (mg/dL) | 9 nA/ (mg/dL) | 9.5 nA/ (mg/dL) | 10 nA/ (mg/dL) | 10.5 nA/ (mg/dL) | 11 nA/ (mg/dL) |
| 400 nA | 1 | 2 | 3 | 4 | 5 | 6 |
| 425 nA | 7 | 8 | 9 | 10 | 11 | 12 |
| 450 nA | 13 | 14 | 15 | 16 | 17 | 18 |
| 475 nA | 19 | 20 | 21 | 22 | 23 | 24 |
| 500 nA | 25 | 26 | 27 | 28 | 29 | 30 |
| 525 nA | 31 | 32 | 33 | 34 | 35 | 36 |

In Equation 3, the output signal(s) $I_{we1}$ or $I_{we2}$ is measured at a particular time (or at a particular interval) $t_c$ during the test measurement sequence. The particular time $t_c$ can be obtained from Equation 4 as follow:

$$t_c=(t_u-t_n)y_1+y_2+t_n \qquad \text{Eq. 4}$$

where $t_c$ is the particular time (in seconds);

$t_u$ includes a specified sampling time (in seconds);

$t_n$ includes a nominal sampling time (in seconds);

$y_1$ includes a dimensionless time multiplier factor derived from Table 2; and $y_2$ includes a time additive component (in seconds) derived from Table 2.

The nominal sampling time $t_n$ may be 2.5 seconds or 5 seconds in certain embodiments. In such embodiments, the specified sampling time $t_u$ can be determined as shown and described in PCT/GB2012/053276, which was incorporated by reference earlier. Specifically, as described in PCT/GB2012/053276, the "specified sampling time" can be determined (from Equation 7 of the same application) by knowing a physical characteristic of the fluid sample, which preferably is defined as an impedance characteristic IC or H. Once the impedance characteristic IC or H of the fluid has been determined (as described in the same application), the "specified sampling time" or $t_u$ can be set as being equal to $x_1 H^{x_2} + x_3$ where $x_1$ is about 4.3e5; $x_2$ is about −3.9; and $x_3$ is about 4.8 (all described in this related application).

The dimensionless time multiplier factor $y_1$ and time additive factor can be obtained from a timing calibration code from 1 to 30, shown here in Table 2. In Table 2, the time multiplier $y_1$ and the time additive factor $y_2$ can be correlated by a single code stored on the biosensor or storage vial 102 and transmitted to the meter, which also has the same array as Table 2 stored in memory so that, for example, if the biosensor has code "8", the meter knows to extract $y_1 \sim 1.05$ and $y_2 \sim (-0.05)$.

TABLE 2

Timing Calibration Code for Appropriate Assay time
Timing calibration code

| $y_2$ or time additive component | $y_1$ - time multiplier factor | | | | |
|---|---|---|---|---|---|
| | 0.85 | 0.95 | 1.05 | 1.15 | 1.25 |
| −0.1 sec | 1 | 2 | 3 | 4 | 5 |
| −0.05 sec | 6 | 7 | 8 | 9 | 10 |
| 0 sec | 11 | 12 | 13 | 14 | 15 |
| 0.05 sec | 16 | 17 | 18 | 19 | 20 |
| 0.1 sec | 21 | 22 | 23 | 24 | 25 |
| 0.15 sec | 26 | 27 | 28 | 29 | 30 |

Alternatively Equation 3 may be expressed in relative terms for the batch slope and batch intercept as Equation 5:

$$G_0 = [I_E - z_2 z_4] \div (z_1 z_2) \qquad \text{Equation 5.}$$

where:

G is glucose concentration reading [mg/dL]

$I_E$ is the current at final assay time [nA]

$z_1$ is the slope [nA/(mg/dL)]—hardcoded in meter and not changeable $z_2$ is the intercept [nA]—hardcoded in meter and not changeable $z_3$ is the slope multiplier [dimensionless]—(see Table 3)

$z_4$ is the intercept multiplier [dimensionless]—(see Table 3)

Where Equation 5 is used for relative calibration correction, Table 3 may be utilized by determining the relative correction while keeping in mind that the batch slope and batch intercept are fixed to a single value in the meter. Consequently, Table 3 provides for the same number of calibration codes (as Table 1) that are linked to the slope multiplier and intercept multiplier except that fixed slope and intercept are stored in the meter and the respective multipliers allow for adjusting the fixed slope and intercepts.

TABLE 3

Calibration Code - Glucose reading (relative correction)
Calibration Code 1

| x4~intercept multiplier | x3~slope multiplier | | | | | |
|---|---|---|---|---|---|---|
| | 0.872 | 0.923 | 0.974 | 1.026 | 1.077 | 1.128 |
| 0.865 | 1 | 2 | 3 | 4 | 5 | 6 |
| 0.919 | 7 | 8 | 9 | 10 | 11 | 12 |
| 0.973 | 13 | 14 | 15 | 16 | 17 | 18 |
| 1.027 | 19 | 20 | 21 | 22 | 23 | 24 |
| 1.081 | 25 | 26 | 27 | 28 | 29 | 30 |
| 1.135 | 31 | 32 | 33 | 34 | 35 | 36 |

Figure 5:
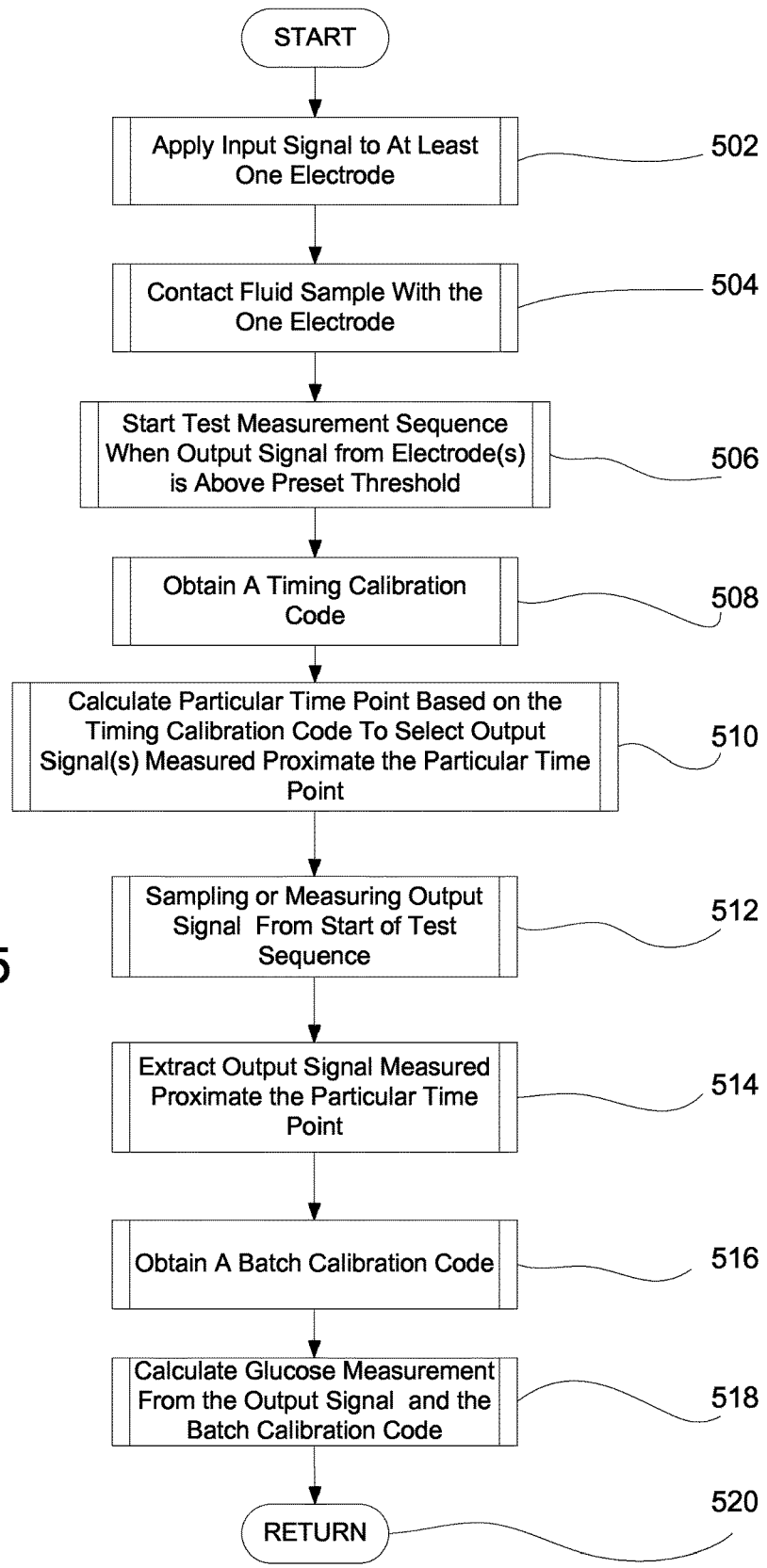
FIG. 5 illustrates a logic diagram representative of one of many techniques that can be gleaned from this disclosure.
Figure 6:
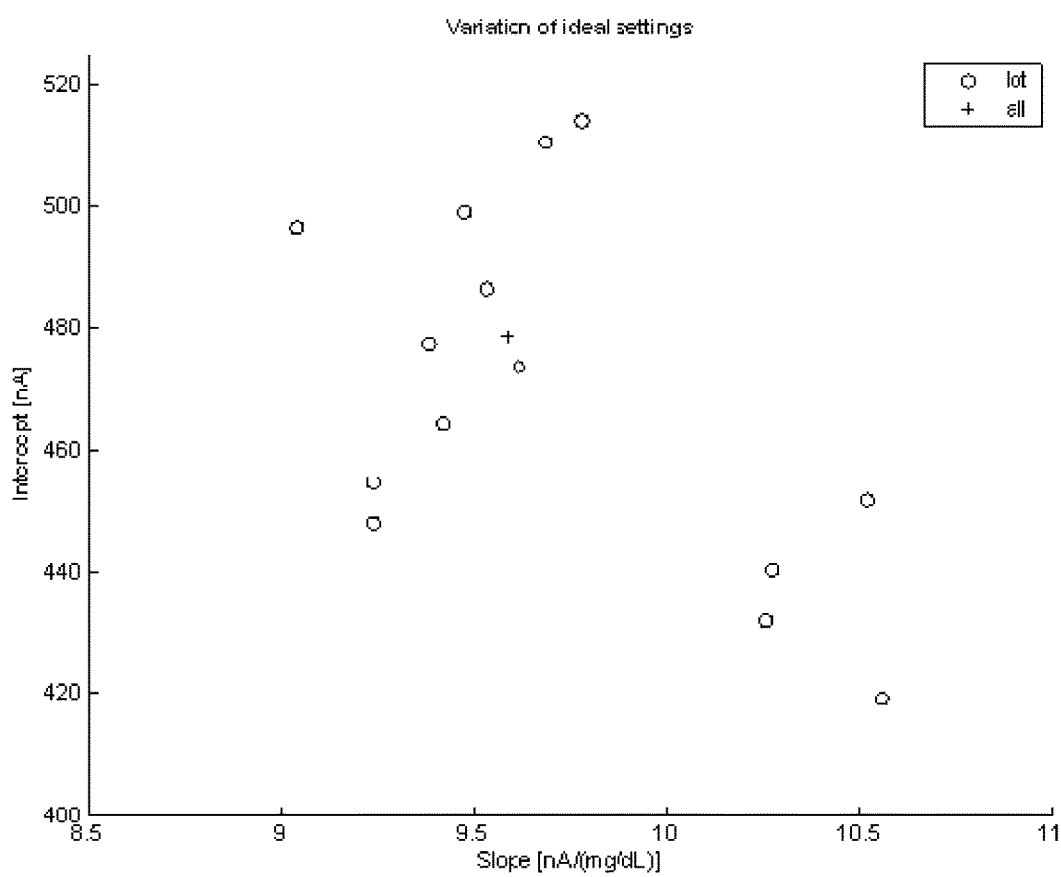
FIG. 6 demonstrates the variation of ideal calibration settings (slope & intercept) with produced lots (i.e., global slope & intercept position is marked as "all").

An explanation of applicant's inventive technique will now be described with reference to FIGS. 4A, 4B and 5. In FIG. 5, a logic diagram 500 is shown for use of the system illustrated in FIGS. 1, 2A, 2B, 3A-3D. Logic 500 starts at step 502 in which an input signal (e.g., electrical voltage of about 400 mV in FIG. 4A) is applied to at least one of the electrodes 12 and 14. Fluid sample 95 can be deposited onto one of the electrodes at step 504. The fluid sample may start an electrochemical reaction which would provide an output signal that can be detected. At step 506, once the signal output from one of the electrodes is above a preset threshold (e.g., above about 0 nA), the process designates this as a start of the test sequence $T_S$ and initiates a timer for the test interval (FIG. 4B at start time "0.0"). The processor can also measure or sample the output signals $I_{we1}$ or $I_{we2}$ from at least one of the working electrodes (12 and 14) at any one of a plurality of time points or positions $T_1, T_2, T_3, \ldots T_N$. As can be seen in FIG. 4B, the time positions can be any time point or interval in the test sequence $T_S$.

For example, the time position at which the output signal is measured can be a single time position (in FIG. 4B) $T_{1.5}$ at 1.5 seconds or an interval 408 (e.g., interval-10 milliseconds or more depending on the sampling rate of the system) overlapping the time position $T_{2.8}$ proximate 2.8 seconds. At step 508 of FIG. 5, the processor obtains a timing calibration code (e.g., Table 2) from the biosensor or the vial 102 containing the biosensor so that a measurement of the output signal could be made proximate a particular sampling time from Equation 4. At step 510, the system determines the particular time $t_c$ based on the "specified sampling time" $t_u$ during the test sequence $T_S$ to measure the output signals from the electrodes. To calculate this "specified sampling time" $t_u$, the processor may measure the impedance characteristic "IC" of the fluid sample, as shown and described in international patent application PCT/GB2012/053276, and noted above (from Equation 7 of the same application) in order to obtain the "specified sampling time" in the related application and this disclosure. The nominal time $t_n$ may be designated as about 2.5 seconds.

Of course, while the steps 508 and 510 are being performed, step 512 can be done at the same time, earlier or later than steps 508 and 510 to measure the signal outputs 402 and 404 over the entire or portions thereof the test sequence $T_S$. Although the signal outputs 402 and 404 (FIG. 4B) are sampled or measured for the entire test sequence, it is usually the case that the signal outputs proximate the particular time $t_c$ will be utilized to calculate the glucose concentration. At step 514, the system may extract the output signals at the particular time $t_c$ (or over an interval overlapping the particular time) from the at least one electrode. At step 516, the system may obtain a batch calibration code from the biosensor or the vial 102 containing the biosensor(s). With the batch calibration code obtained in step 516, the system can look up its memory to determine the corresponding batch slope $z_1$ and batch intercept $z_2$ correlated to the particular calibration code. At step 518, the system utilizes both of these values ($z_1$ and $z_2$) along with the measured output signal $I_E$ at the particular time $t_c$ to calculate or determine the glucose concentration in the fluid sample (which fluid sample may be physiological fluid such as blood, tears, sweat or synthetic fluid such as control solution).

To recap, the method describes and shown in flow chart 500 allow for applicant to obtain an accurate glucose concentration by: contacting a fluid sample with the at least one electrode to start a test measurement in step 504; obtaining a timing calibration code at step 508; calculating a particular time point ($t_c$) from the start of the test measurement for sampling a signal output of the sample based on the timing calibration code at step 510; applying a signal input to the sample at step 502; measuring a signal output from the sample from the start of a test measurement at step 512; determining at least one particular signal output proximate at least the particular time point after the start of the test measurement at step 514; obtaining a calibration code at step 516; and calculating a glucose concentration from the at least one particular signal output and the calibration code at step 518. In short, applicant has devised a technique that utilizes two calibration codes: one for time calibration and one for batch calibration.

As an example of an analyte calculation (e.g., glucose) for strip 100 (FIGS. 3A-3F and its variants in the Related Applications), it is assumed, for this example only, that the biosensor 100 has an RFID tag 101 embedded into the biosensor such that both the calibration code and timing assay calibration code are stored in the RFID tag 101 for later retrieval by the meter and its associated reader 322. Examples of such RFID systems are well known and described at, for example, US Patent Application Publication Nos. 20100148972 and US20120305419. Alternatively, a micro bar-code can be imprinted on the biosensor or the vial for later reading and retrieval by the meter. In this example, it is assumed that the batch calibration code is "15" and the timing calibration code is "23". For calibration code "15", the meter via its processor can determine from its memory that the batch slope $z_1$ is therefore 9.5 nA/(mg/dL) and the batch intercept $z_2$ is therefore 450 nA (Table 1). For timing calibration code "23", the meter can determine from its memory that the time multiplier factor $y_1$ in Equation 4 is about 1.05 and the time additive component $y_2$ in Equation 4 is about 0.1 second. For this example, it is also assumed that the nominal time is about 5 seconds and the specified sampling time based on the sensed impedance of the fluid is about 5.5 seconds. From Equation 4, the particular time $t_c$ for the system to sample the fluid is as follows:

$$t_c = (t_u - t_n)y_1 + y_2 + t_n$$

and $t_u$=2 seconds;
$t_n$=2.5 seconds;
$y_1$=1.05; and
$y_2$=0.1 second
$t_c$=2.1 seconds Using the particular sampling time $t_c$ of about 2.1 seconds, the system extracts the measured output signal at step 514, which in this example for the first working electrode 12 is about 1600 nanoamperes (measured at about 2.1 seconds from the start of test sequence) whereas the output signal at 406 for the second working electrode 14 is about 1300 nanoamperes and the calibration code of the test strip indicates that the batch intercept $z_2$ is about 450 nanoamperes (also measured at about 2.1 seconds from the start) and the batch slope $z_1$ is about 9.5 nanoamperes/mg/dL.

$$G_0 = [(1600+1300)-450]/9.5 \text{ and therefore, } G_0 \sim 258 \text{ mg/dL.} \quad \text{From Equation 3;}$$

It is noted here that the examples have been given in relation to a biosensor 100 which has two working electrodes (12 and 14 in FIGS. 3A-3D (and its variants in the Related Applications) such that the measured signals from respective working electrodes have been added together to provide for a total measured current $I_E$, the signal resulting from only one of the two working electrodes can be multiplied by two in a variation of test strip 100 where there is only one working electrode (either electrode 12 or 14). Instead of a total measured signal, an average of the signal from each working electrode can be used as the total measured signal $I_E$ for Equation 3, described herein, and of course, with appropriate modification to the operational coefficients (as known to those skilled in the art) to account for a lower total measured signal $I_E$ than as compared to an embodiment where the measured signals are added together. Alternatively, the average of the measured signals can be multiplied by two and used as $I_E$ in Equations 3.3, without the necessity of deriving the operational coefficients as in the prior example. It is noted that the analyte (e.g., glucose) concentration here is not corrected for any physical characteristic (e.g., hematocrit value) and that certain offsets may be provided to the signal values $I_{we1}$ and $I_{we2}$ to account for errors or delay time in the electrical circuit of the meter 200. Temperature compensation can also be utilized to ensure that the results are calibrated to a referential temperature such as for example room temperature of about 20 degrees Celsius.

Principles of applicant's invention have been proven with respect to the following non-limiting example.

Example

In this example, 14 lots of the test strip 100 were obtained and divided into two categories, the first category labeled as "no calibration code use" and the second category labeled as "calibration-code used". For the second category of the strips that utilized calibration parameters, the calibration parameters were determined for "slope" or $z_1$; "intercept" or $z_2$; "multiplier" or $y_1$; and "additive time" or y2. These calibration parameters for each lot are summarized in Table 4.

TABLE 4

Optimal settings for coded parameters in the Example
Table 4 - Cal-Code values per lot

| Lot | Slope $z_1$ | Intercept $z_2$ | Time Multiplier - $y_1$ | Additive Time - $y_2$ |
|---|---|---|---|---|
| 1 | 10.256 | 431.885 | 0.983 | 0.061 |
| 2 | 10.558 | 419.002 | 1.019 | 0.127 |
| 3 | 10.272 | 440.351 | 0.841 | −0.058 |
| 4 | 10.521 | 451.550 | 0.886 | −0.087 |
| 5 | 9.421 | 464.196 | 1.044 | 0.023 |
| 6 | 9.239 | 454.537 | 0.947 | 0.051 |
| 7 | 9.039 | 496.549 | 0.991 | 0.082 |
| 8 | 9.779 | 513.981 | 1.123 | −0.025 |
| 9 | 9.616 | 473.527 | 1.123 | 0.047 |
| 10 | 9.532 | 486.272 | 1.140 | 0.008 |
| 11 | 9.239 | 447.782 | 1.154 | 0.126 |
| 12 | 9.688 | 510.382 | 1.154 | −0.065 |
| 13 | 9.475 | 499.040 | 1.203 | −0.006 |
| 14 | 9.385 | 477.362 | 1.180 | 0.013 |

Glucose test measurements were made using test strips from these lots and the results from each lot for each of the two categories were collated in Table 5. Table 5 shows the two categories ("no calibration coding" and "calibration coding used") in the two main columns indexed by the lot sequences 1-14 in the first column. For each row of the table, the numbers in each of the second through fifth represent the percentage of samples that meet the thresholds in the first row, i.e., within "15 mg/dL" as compared to referential YSI for glucose results less than 100 mg/dL or within ±"15%" as compared to referential YSI for glucose results greater than or equal to 100 mg/dL for each of the two categories.

TABLE 5

Results of Example
Table 5: Performance Results per lot

|  | No-Calibration Coding % samples within | Calibration Coding | No-Calibration Coding % samples within | Calibration Coding |
| --- | --- | --- | --- | --- |
|  | ±15 mg/dL of reference for results less than 100 mg/dL | ±15 mg/dL of reference for results less than 100 mg/dL | ±15% to reference for results ≥100 mg/dL | ±15% to reference for results ≥100 mg/dL |
| 1 | 100% | 100 | 91.9 | 95.9 |
| 2 | 98.9 | 98.9 | 90.6 | 99.1 |
| 3 | 99.7 | 99.7 | 98.1 | 100 |
| 4 | 99.7 | 100 | 98.7 | 100 |
| 5 | 99 | 99.3 | 94.8 | 93 |
| 6 | 97.8 | 99.1 | 90.5 | 94.5 |
| 7 | 97.4 | 97.4 | 83 | 93.1 |
| 8 | 96.6 | 98.5 | 93.6 | 94.2 |
| 9 | 99.8 | 100 | 95.6 | 95.3 |
| 10 | 99.8 | 99.6 | 98.9 | 98.3 |
| 11 | 97.3 | 100 | 92.6 | 98.6 |
| 12 | 96.3 | 98.1 | 96.5 | 97.1 |
| 13 | 97.7 | 97.9 | 97 | 92.2 |
| 14 | 97.8 | 96.4 | 96.5 | 94.4 |

A review of the results from Table 5 confirms the advantages of applicant's dual coding technique for both batch and time. In particular, for glucose concentration less than 100 mg/dL, out of 14 lots, 9 lots that utilized calibration coding described generally herein (i.e., lots 4-9, 11-13) had higher percentages of results within ±15 mg/dL of referential YSI; and only two lots that did not use calibration coding (lots 10 and 14) exceeded their counterparts that use calibration coding but even so these were not by much (99.8% versus 99.6% for lot 10 and 97.8% versus 96.4% for lot 14).

For glucose results at 100 mg/dL or greater, the calibration coded lots showed greater number of lots that have higher percentages (lots 1-4, 6-8, 11, and 12) to the non-coded lots. It is noted that the non-coded lots do have four lots (lots 5, 9, 10, 13, and 14) that exceeds the calibration coded lots but, again, it should be noted that the magnitude of differences for each lot was not considered to be a substantial advantage over the coded calibration lots.

Figure 7:
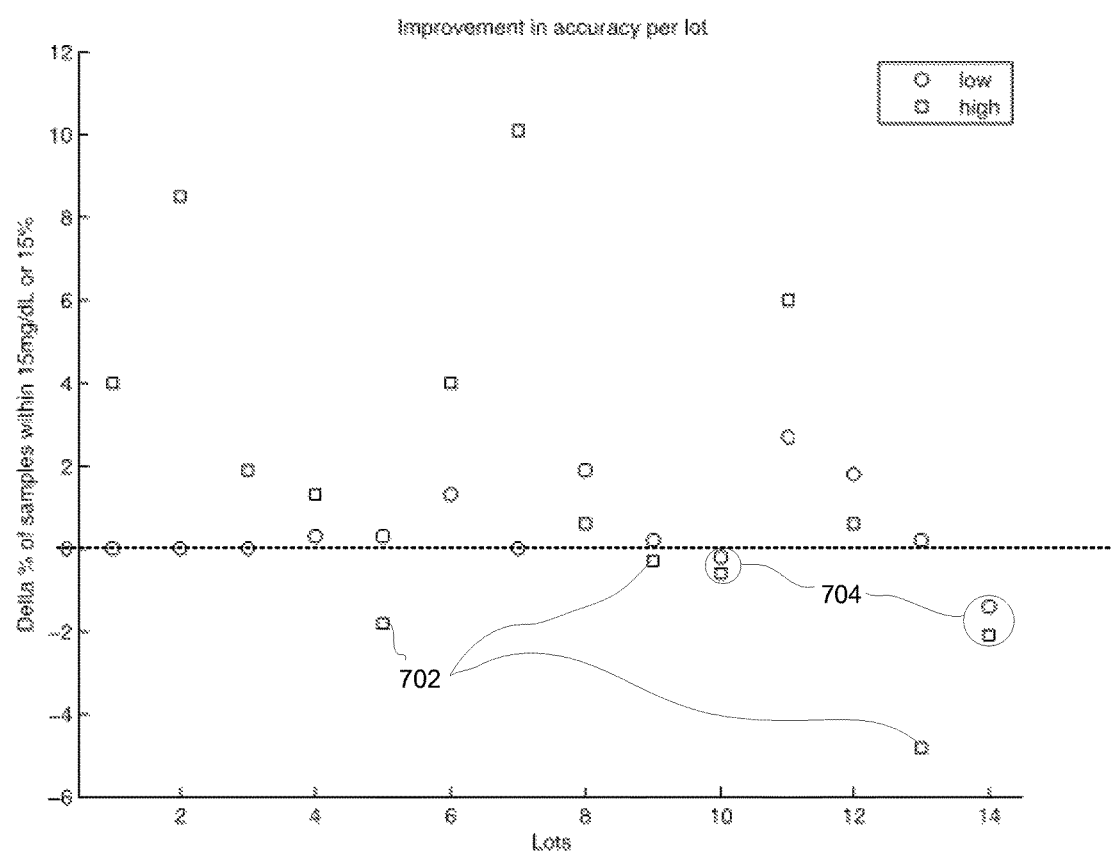
FIG. 7 demonstrates the difference in achieved accuracy per lot (i.e., positive shift equates to improvement and negative shift indicates detrimental effect).

FIG. 7 illustrates graphically the improvements for lots 1-14. In FIG. 7, the dashed line at 0% signifies no improvement and any points above the dashed line indicates percent improvements and any points below the dashed line indicates detriment. Specifically, it is noted that there were three lots that experienced a detrimental effects at glucose results greater than or equal to 100 mg/dL at 702. There were two lots that experienced detrimental effects at both low values (below 100 mg/dL) and high values (100 mg/dL or greater), indicated at 704. On the whole, however, at least half of the lots showed clear improvements by use of the dual batch and time calibration codlings of applicant.

In summary, it can be seen in FIG. 5 that there are wide variations in the calibration parameters (slopes and intercepts) in the produced lots of biosensors. In contrast, embodiments of this invention, as shown and described in relation to FIGS. 1-5, Tables 1-3 ensures a more reproducible product being utilized by patients in the field. This is achieved not by complex and costly process and material control at point of manufacture but by establishing the deviation from a gold standard product setting and passing this information to the point of testing for the patients or users. Overall batch-to-batch variability is addressed and minimized (shown by Table 5 and FIG. 7) by virtue of the dual-calibration coding exemplarily described in relation to FIGS. 1-5 and Tables 1-3.

While the invention has been described in terms of particular variations and illustrative figures, those of ordinary skill in the art will recognize that the invention is not limited to the variations or figures described. In addition, where methods and steps described above indicate certain events occurring in a certain order, it is intended that certain steps do not have to be performed in the order described but in any order as long as the steps allow the embodiments to function for their intended purposes. Therefore, to the extent there are variations of the invention, which are within the spirit of the disclosure or equivalent to the inventions found in the claims, it is the intent that this patent will cover those variations as well.

What is claimed is:

1. A method for determining a glucose concentration of a fluid sample applied to a biosensor from a lot of biosensors, the lot of biosensors being calibration coded with a timing calibration code and a batch calibration code, wherein the calibration codes are selected to improve glucose concentration measurements as compared to referential data, the method comprising the steps of:
    applying an input signal to at least one electrode of the biosensor;
    contacting fluid sample with the at least one electrode;
    initiating a test measurement sequence only when an output signal from the electrode is above a predetermined threshold;
    obtaining a timing calibration code of the biosensor, the timing calibration code being for determining when to start sampling the output signal and correlated to a time multiplier factor and a time additive component;
    determining a particular time point during the test sequence based on the time multiplier factor and the time additive component of the timing calibration code in order to select output signals measured proximate the particular time point;
    sampling or measuring output signals from the start of the test sequence;
    extracting an output signal proximate the determined particular time point;
    obtaining a batch calibration code of the biosensor based on manufacturing variations thereof; and
    calculating an analyte concentration from the extracted output signal at the particular time point and the batch calibration code.

2. The method according to claim 1, further comprising:
    measuring a hematocrit level of the sample; and
    using the measured hematocrit level, determining a specified sampling time;
    using the timing calibration code, the specified sampling time and a predetermined nominal sampling time to determine the particular time point.

3. The method according to claim 2, wherein the particular time point is obtained using the relationship $t_c=(t_u-t_n)y_1+y_2+t_n$, wherein

- $t_c$ is the particular time point;
- $t_u$ is the specified sampling time;
- $t_n$ is the predetermined nominal time;
- $y_1$ is the time multiplier factor obtained from the timing calibration code; and
- $y_2$ is the time additive component obtained from the timing calibration code, in which the predetermined nominal time is 2.5 seconds from the initiation of the test measurement.

4. The method according to claim 2, wherein the hematocrit level of the sample is determined from an impedance characteristic.

5. The method according to claim 1, in which the method further comprises:
- obtaining a slope multiplier and an intercept multiplier from the batch calibration code;
- determining the glucose concentration using the slope multiplier, the intercept multiplier and the output signal at the particular time point.

6. The method according to claim 3, wherein the obtaining of the timing calibration code comprises transmitting of the time multiplier factor and the time additive component from one of a storage container for the biosensor or the biosensor itself to a test meter.

7. The method according to claim 5, wherein the obtaining of the batch calibration code comprises transmitting of the slope multiplier and the intercept multiplier from one of a storage container for the biosensor or the biosensor itself to a test meter.

* * * * *